US 7,264,816 B2

(12) United States Patent
Foley et al.

(10) Patent No.: US 7,264,816 B2
(45) Date of Patent: Sep. 4, 2007

(54) VIRULENT SYSTEMIC FELINE CALICIVIRUS

(75) Inventors: Janet E. Foley, Davis, CA (US); Kate Hurley, Davis, CA (US); Niels C. Pedersen, Winters, CA (US); Amy Poland, Vacaville, CA (US)

(73) Assignee: The Regents of the University of California, Oakland, CA (US)

( * ) Notice: Subject to any disclaimer, the term of this patent is extended or adjusted under 35 U.S.C. 154(b) by 282 days.

(21) Appl. No.: 10/769,531

(22) Filed: Jan. 30, 2004

(65) Prior Publication Data

US 2004/0259225 A1    Dec. 23, 2004

Related U.S. Application Data

(63) Continuation-in-part of application No. 10/388,837, filed on Mar. 14, 2003.

(51) Int. Cl.
    *C12N 7/00* (2006.01)
(52) U.S. Cl. .................. 424/216.1; 435/235.1
(58) Field of Classification Search ..................... None
    See application file for complete search history.

(56) References Cited

U.S. PATENT DOCUMENTS

| | | | |
|---|---|---|---|
| 3,937,812 A | 2/1976 | Bittle et al. | |
| 3,944,469 A | 3/1976 | Bittle et al. | |
| 3,992,520 A | 11/1976 | Gwatkin | |
| 4,522,810 A * | 6/1985 | Pedersen ................ | 424/216.1 |
| 4,795,634 A | 1/1989 | Grimes et al. | |
| 5,716,822 A | 2/1998 | Wardley et al. | |
| 5,718,901 A | 2/1998 | Wardley et al. | |
| 5,785,968 A | 7/1998 | Kimachi et al. | |
| 5,916,768 A | 6/1999 | Dean | |
| 5,989,550 A | 11/1999 | Harris et al. | |
| 6,231,863 B1 | 5/2001 | Colau et al. | |
| 6,355,246 B1 | 3/2002 | Kruger et al. | |

OTHER PUBLICATIONS

Pedersen et al., An isolated epizootic of hemorrhagic-like fever in cats caused by a novel and highly virulent strain of feline calicivirus. Veterinary Microbiology, 2000, vol. 73, p. 281-300.*
Afzalpurkar, Abhijit, et al.; "Induction of native protein reactive antibodies by immunization with peptides containing linear B-cell epitopes defined by anti-porcine ZP3β monoclonal antibodies"; *Journal of Reproductive Immunology* 1997 pp. 113-125 vol. 33.
Bagavant, Harini, et al.; "Autoimmune Ovarian Inflammation Triggered by Proinflammatory (Th1) T Cells is Compatible with Normal Ovarian Function in Mice"; *Biology of Reproduction* 1999 pp. 635-642 vol. 61.
Foster, James, A., et al.; "AM67, a Secretory Component of the Guinea Pig Sperm Acrosomal Matrix, Is Related to Mouse Sperm Protein sp56 and the Complement Component 4-binding Proteins"; *The Journal of Biological Chemistry* 1997 pp. 12714-12722 vol. 272 No. 19.
Johnson, R.P., "Antigenic Change in Feline Calicivirus During Persistent Infection," *Can J Vet Res.*, 56:326-330, (1992).
Pederson, N.C. et al., "An isolated epizootic of hemorrhagic-like fever in cats caused by a novel and highly virulent strain of feline calicivirus," *Veterinary Microbiology*, 73:281-300, (2000).
Prasad, S.V., et al.; "Molecular biology approaches to evaluate species variation in immunogenicity and antigenicity of zona pellucida proteins"; *Journal of Reproduction and Fertility Supplement* 1996 pp. 143-149 vol. 50.
Reubel, G.H. et al., "Acute and Chronic Faucitis of Domestic Cats- A Feline Calicivirus-Induced Disease," *Veterinary Clinics of North America: Small Animal Practice*, 22(6):1347-1360, (1992).
Studdert, M.J., "Calicivirus- Brief Review,9" *Archives of Virology*, 58:157-191, (1978).
<http://www.pandecats.com/x/calici_outbreak_warning.htm> "Outbreak of Calicivirus in Los Angeles, California," visited on Jun. 17, 2003, 2 pages.
<http://www.vetmed.ucdavis.edu/CCAH/Prog-ShelterMed/news. htm> "Focal outbreak of an unusually virulent strain of feline calicivirus," visited on Jun. 17, 2003, 4 pages.
<http://www.vetmed.ucdavis.edu/whatsnew/article.cfm?id=1178> "School of Veterinary Medicine investigates rare virus outbreak in cats," visited on Jun. 17, 2003, 2 pages.
L11000/PIGZP3 Genbank entry Oct. 7, 1994 polynucleotide sequence encoding ZP protein.

* cited by examiner

*Primary Examiner*—Bruce R. Campell
*Assistant Examiner*—Agnieszka Boesen
(74) *Attorney, Agent, or Firm*—Townsend & Townsend & Crew LLP

(57) ABSTRACT

The present invention relates to a vaccine for immunization against a viral infection caused by a virulent systemic feline calicivirus (VS-FCV), a novel, atypical and unusually virulent form of a calicivirus that results in a highly contagious and fatal hemorrhagic fever syndrome. The present invention further encompasses methods of immunizing cats against particular strains of VS-FCV.

10 Claims, 2 Drawing Sheets

```
                  1                                                           50
SEQ ID NO: 1   MCSTCANVLK YYDWDPHFKL VINPNNFLSV GFCSNPLMCC YPELLPEFGT
SEQ ID NO: 2   MCSTCANVLK YYGWDPHFRL TINPNRFLSV GFCDKPLICC YPELLPEFGT
SEQ ID NO: 3   MCSTCANVLK YYDWDPLFRL IINPNKFLSV GFCDNPLMCC YPELLPEFGT
SEQ ID NO: 4   MCSTCANVLK YYNWDPHFRL VINPNKFLSV GFCDNPLMCC YPELLPEFGT 51                                                          100
SEQ ID NO: 1   VWDCDRSPLE IYLESILGDD EWASTFDAVD PVVPPMHWGA AGKIFQPHPG
SEQ ID NO: 2   VWDCDQSPLQ IYLESILGDD EWSSTYDAID PCVPPMHWDE AGKIFQPHPG
SEQ ID NO: 3   VWDCDQSPLQ IYLESILGDD EWESTYEAVD PVVPPMHWDT AGKIFQPHPG
SEQ ID NO: 4   VWDCDQSPLQ IYLESILGDD EWSSTYEAID PCVPPMHWDE AGKIFQPHPG 101                                                         150
SEQ ID NO: 1   VLMHHLIGKV AAGWDPDLPL IRLEADDGSI TAPEQGTMVG GVIAEPSAQM
SEQ ID NO: 2   VLMHHLINEV AKGWDPSLPN FRLEADDGSI TTPEQGTMVG GVIAEPSSQM
SEQ ID NO: 3   VLMHYLIGEV AKAWDPNLPL FRLEADDGSI TTPEQGTMVG GVIAEPSAQM
SEQ ID NO: 4   VLMHHIIGEV AKAWDPNLPN FRLEADDGSI TTPEQGTTVG GVIAEPSVQM 151                                                         200
SEQ ID NO: 1   STAADMATGK SVDSEWEAFF SFHTSVNWST SETQGKILFK QSLGPLLNPY
SEQ ID NO: 2   SAAADMATGK SVDSEWEAFF SFHTSVNWST SETQGKILFK QSLGPLLNPY
SEQ ID NO: 3   STAADMATGK SVDSEWEAFF SFHTSVNWST SETQGKILFK QSLGPLLNPY
SEQ ID NO: 4   SAAADMATGK SVDSEWEAFF SFHTSVNWST SETQGKILFK QSLRPLLNPY 201                                                         250
SEQ ID NO: 1   LEHLAKLYVA WSGSIEVRFS ISGSGVFGGK LAAIVVPPGV DPVQSTSMLQ
SEQ ID NO: 2   LSHLAKLYVA WSGSIEVRFS ISGSGVFGGK LAAIVVPPGI DPVQSTSMLQ
SEQ ID NO: 3   LEHLSKLYVA WSGSVEVRFS ISGSGVFGGK LAAIVVPPGV EPVQSTSMLQ
SEQ ID NO: 4   LTHLAKLYVA WSGSIEVRFS ISGSGVFGGK LAAIVVPPGI EPIQSTSMLQ 251                                                         300
SEQ ID NO: 1   YPHVLFDARQ VEPVIFCLPD LRSTLYHLMS DTDTTSLVIM VYNDLINPYA
SEQ ID NO: 2   YPHVLFDARQ VEPVIFSIPD LRSTLYHFMS DTDTTSLAIM VYNDLINPYA
SEQ ID NO: 3   YPHVLFDARQ VEPVIFSIPD LRSSLYHLMA DPDPTYLVIM VYNDLINPYA
SEQ ID NO: 4   YPHVLFDARQ VEPVIFTIPD LRSTLYHLMA DPEPTSLVIM IYNDLINPYA 301                                                         350
SEQ ID NO: 1   NDANSSGCIV TVETKPGPDF KFHLLKPPGS MLTHGSIPSD LIPKTSSLWI
SEQ ID NO: 2   NDSNSSGCIV TVETKPGPDF KFHLLKPPGS MLTHGSVPSD LIPRSSSYWT
SEQ ID NO: 3   NDSNSSGCIV TVETKPGPDF KFHLLKPPGS MLTHGSVPSD LIPKSSSLWI
SEQ ID NO: 4   NDSNSSGCIV TVETKPGPDF KFHLLKPPGS MLTHGSVPCD LIPKSSSLWI
```

FIGURE 1

```
              351                                                                400
SEQ ID NO: 1  GNRYWSDITD  FVIRPFVFQA  NRHFDFNQET  AGWSTPRFRP  ISVTITEQNG
SEQ ID NO: 2  GNRHWTDITG  FVIRPFVFQA  NRHFDFNQET  AGWSSPRFRP  ISINISVEKA
SEQ ID NO: 3  GNRHWTDITD  FVIRPFVFQA  NRHFDFNQET  AGWSTPRYRP  MTINISQKKG
SEQ ID NO: 4  GNRFWSDITD  FVIRPFVFQA  NRHFDFNKET  AGWSTPRFRP  ITVTISQKEG 401                                                                450
SEQ ID NO: 1  AKLGIGVATD  YIVPGIPDGW  PDTTIPGELI  PAGDYAITNG  TGNDITTATG
SEQ ID NO: 2  AKLGTGVATD  YIVPGIPDGW  PDTTIPEKLT  PAGDYAIVDG  SGNDITTKDK
SEQ ID NO: 3  ERLGIGIATD  YIVPGIPDGW  PDTTIPEELT  PAGDYAIVNG  T.SDIATKAQ
SEQ ID NO: 4  EMLGIGVATD  YIVPGIPDGW  PDTTIPNKLI  PAGDYAITNQ  SGNDIQTKEE 451                                                                500
SEQ ID NO: 1  YDTADIIKNN  TNFRGMYICG  SLQRAWGDKK  ISNTAFITTA  TLDGDNNNKI
SEQ ID NO: 2  YESADVIKNN  TNFRGMYICG  SLQRAWGDKK  ISNTAFITTG  TVK...DNSI
SEQ ID NO: 3  YEAATIITNN  TNFKSMYICG  SLQRAWGDKK  ISNTAFITTG  KVEG...NKI
SEQ ID NO: 4  YESAMIISNN  TNFKSMYICG  SLQRAWGNKK  VSNTAFITTA  TVK...ENKL 501                                                                550
SEQ ID NO: 1  NPCNTIDQSK  IVVFQDNHVG  KKAQTSDDTL  ALLGYTGIGE  QAIGSDRDRV
SEQ ID NO: 2  IPSNTIDQTK  ITVFQDTHVG  HDPQTSDDTL  ALLGYTGIGE  EAIGADRDRV
SEQ ID NO: 3  TPSNKIDPTM  IAVFQDNHVN  LEVQTSDVTL  ATLGYTGIGE  EAIGADREKV
SEQ ID NO: 4  IPSNTIDQTK  IAIFQDNHVN  RDVQTSDDTL  ALLGYTGIGE  EAIGADREKV 551                                                                600
SEQ ID NO: 1  VRISTLPETG  ARGGNHPIFY  KNSIKLGYVI  RSIDVFNSQI  LHTSRQLSLN
SEQ ID NO: 2  VRISVLPETG  ARGGNHPIFY  RNSIKLGYVL  KDIDVFNSQI  LHTSKQLSLN
SEQ ID NO: 3  VRISVLPETG  ARGGNHPIYY  KNKMKLGYVI  DGIDVFNSQI  LHTSRQLSLN
SEQ ID NO: 4  VRIGVLPEAG  ARGGNHPIFY  RNSMKLGYVI  KSIDVFNSQI  LHTSRQLSLN 601                                                                650
SEQ ID NO: 1  HYLLPPDSFA  VYRIIDSNGS  WFDIGIDSDG  FSFVGVSGFG  KLEFPLSASY
SEQ ID NO: 2  HYLLSPDSFA  VYRITDSNGS  WFDIGIDNDG  FSFVGVSYIG  NLEFPLTASY
SEQ ID NO: 3  NYLLPPDSFA  VYRITDANGS  WFDIGIDSDG  FSFVGVSSIG  KLISPLSASY
SEQ ID NO: 4  NYLLSPDSFA  VNPTIDSNGS  WWSIGSDIDS  RILVNVSTRG  KKEFPLRSFC 651                    671
SEQ ID NO: 1  MGIQLAKIRL  ASNIRSPMTK  L
SEQ ID NO: 2  MGIQLAKIRL  ASNIRSGMVK  I
SEQ ID NO: 3  MGIQLAKIRL  ASNIRSSMTK  L
SEQ ID NO: 4  SENQSGKIRS  ASFIKTTRSK  L
```

FIGURE 1 (CONTINUED)

VIRULENT SYSTEMIC FELINE CALICIVIRUS

CROSS-REFERENCES TO RELATED APPLICATIONS

This application is a continuation-in-part of application Ser. No. 10/388,837, filed on Mar. 14, 2003, the disclosure of which is incorporated by reference herein in its entirety.

BACKGROUND OF THE INVENTION

Feline calicivirus (FCV) is a common pathogen found in cats. This virus is often detected in multiple cat environments such as shelters and catteries. Feline calicivirus (FCV) infection can cause a variety of manifestations and symptoms including fever, upper respiratory signs, acute or chronic oral disease, limping, and occasionally pneumonia. Vaccination with an attenuated live virus against FCV is widely practiced, and affords moderate protection against acute disease caused by many, but not all, strains of calicivirus. Cats in FCV endemic populations may shed FCV in ocular and nasal discharge, saliva, and feces without showing clinical signs of infection. Such carrier cats may serve as a source of infection for others. In the past, feline caliciviral infection was not usually fatal, however, when death occurred it was most often due to pneumonia or severe upper respiratory infection in young kittens.

FCV infection and disease occur in acute and chronic forms (Studdert, M. J. (1978) *Arch. Virol.,* 58:157-191; Reubel et al., (1992) *Vet. Clin. No. Am. Small Anim. Pract.,* 22:1347-1360), wherein the manifesting signs of acute disease depend on the route (e.g., oral, aerosol) and the strain of virus. The disease may differ in severity, with more virulent strains causing fever; depression; dyspnea; pneumonia; and vesicles and ulcers of the tongue, hard palate and nostrils. Lower virulence strains are less likely to affect the lungs, although other signs are similar. Most FCV carriers are asymptomatic, however, a small proportion will develop a distinct disease syndrome known as chronic plasmacytic or lymphocytic stomatitis or chronic ulceroprolifereative stomatitis (Reubel et al. (1992) supra). This chronic oral disease is progressive and difficult to treat and is perhaps the most prevalent clinical manifestation of FCV as known. Although recognized strains of FCV have not been associated with significant acute mortality, the calicivirus genome is known to be highly mutable (Johnson, R. P., (1992) *Can. J. Vet. Res.,* 56:326-330). Thus, more highly virulent strains may arise at any time.

SUMMARY OF THE INVENTION

The present invention relates to a vaccine and methods for immunization against a viral infection caused by a virulent systemic feline calicivirus, designated VS-FCV, a novel, atypical and unusually virulent form of a calicivirus that results in a highly contagious and fatal hemorrhagic fever syndrome.

One aspect of the present invention provides an isolated virulent systemic calicivirus (VS-FCV), wherein the virus causes a highly contagious hemorrhagic fever syndrome in cats with symptoms selected from the group consisting of high fever, edema, ulceration, hair loss, nasal and ocular discharge, anorexia, depression, and death, wherein treatment of the cats with antiserum against FCV-F9 achieves substantially no protection against infection with VS-FCV.

Another aspect of the present invention provides an isolated virulent systemic calicivirus (VS-FCV), wherein the virus comprises a capsid protein including an amino acid residue selected from the group consisting of lysine (K) at amino acid position 448; glutamic acid (E) at amino acid position 452; lysine (K) at amino acid position 581; and aspartic acid (D) at amino acid position 581. Optionally, the capsid protein has asparagine (N) at amino acid position 394, wherein the asparagine (N) includes a glycosylation site. Examples of the VS-FCV include, but are not limited to, strains such as FCV-Kaos, FCV-Ari and FCV-Bellingham.

Another aspect of the invention provides an isolated virulent systemic calicivirus (VS-FCV) comprising a capsid protein, wherein lysine (K) is at amino acid position 448; glutamic acid (E) is at amino acid position 452; and lysine (K) or aspartic acid (D) is at amino acid position 581. Optionally, the capsid protein has an asparagine (N) at amino acid residue 394 which includes a glycosylation site.

The invention further encompasses an immunogenic composition for immunization against a viral infection caused by a virulent systemic feline calicivirus (VS-FCV), wherein the composition comprises an immunologically effective amount of the VS-FCV and a physiologically acceptable carrier. Optionally, the composition includes an adjuvant. The VS-FCV strains may be killed, attenuated, or partially inactivated.

Still another aspect of the invention provides for a method of immunizing a cat against a virulent systemic feline calicivirus (VS-FCV) which comprises administering to the cat an immunologically effective dose of the composition comprising an immunologically effective amount of the VS-FCV and a physiologically acceptable carrier. The vaccine may be administered through various routes, including but not limited to, oronasally, subcutaneously, and intramuscularly.

The invention also contemplates a method of detecting a virulent systemic feline calicivirus (VS-FCV) antibody in a biological sample. The method includes contacting the biological sample with an antigen of a VS-FCV and detecting the formation of an immune complex. Optionally, the antigen is a whole virus.

Another aspect of the invention provides an isolated virulent systemic calicivirus (VS-FCV) comprising a capsid protein, wherein lysine (K) is at amino acid position 399; threonine (T) is at amino acid position 430; valine (V) is at amino acid position 438; lysine (K) is at amino acid position 448; glutamic acid (E) is at amino acid position 452; aspartic acid (D) is at amino acid position 581; and wherein the VS-FCV further comprises a glycosylation site including an asparagine at amino acid position 394. Examples of the VS-FCV include, but are not limited to, strains such as FCV-Kaos and FCV-Ari.

BRIEF DESCRIPTION OF THE DRAWINGS

The present invention is best understood when read in conjunction with the accompanying figures which serve to illustrate the preferred embodiments. It is understood, however, that the invention is not limited to the specific embodiments disclosed in the figures.

FIG. 1 depicts an optimal alignment of the capsid proteins m86379 (SEQ ID NO: 1); FCV-Ari (SEQ ID NO: 2); FCV-Kaos (SEQ ID NO: 3); and FCV-Bellingham (SEQ ID NO: 4).

DETAILED DESCRIPTION OF THE INVENTION

Definitions

A "virulent systemic feline calicivirus" (FCV) refers to an, atypical, unusually virulent and highly contagious form of feline calicivirus (FCV) that results in a hemorrhagic fever syndrome in cats. A VS-FCV strain of the invention cannot be neutralized by antibodies to universal vaccine strains (e.g., FCV-F9), thus, treatment of cats with antiserum against FCV-F9 achieves negligible protection against infection with VS-FCV. A VS-FCV of the invention can be identified by the relative inability of antiserum against FCV-F9 to neutralize virus in a standard in vitro assay as described for example in Pedersen et al. *Vet. Microbiol.* (2000) 73:281-300. A virus neutralizing antibody assay suitable for this purpose is described in detail below. Briefly, virus neutralizing titers are determined by reacting serial dilutions of serum from a cat vaccinated with FCV-F9 with a constant amount of an FCV to be tested. Cyotpathic effect (CPE) against Crandell feline kidney cells (CrFK) is used to determine viral infectivity. The last dilution containing any detectable CPE was read as endpoint. A CPE at a dilution of less than 1:16 of anti-FCV-F9 antiserum of an isolate capable of causing fatal systemic disease, is an indication that the FCV is a VS-FCV of the invention.

The term "substantially no protection" means that when a cat is treated with antiserum against FCV-F9 or an antiserum similar to FCV-F9, it provides no protective immunity against infection with VS-FCV, i.e., the cat will still exhibit one or more symptoms that define VS-FCV infection or the VS-FCV is able to replicate within the cat.

The term "amino acid position", when used in the context of amino acid substitutions that characterize VS-FCV isolates of the invention, is used to refer to the position of a particular residue in a capsid protein when optimally aligned with the capsid protein sequence of SEQ ID NO: 1, which is NCBI Accession Numbers M86379.1 or GI:323877 (see also, Carter et al., *Arch. Virol.*, 122(3-4):223-235 (1992). An exemplary alignment of capsid amino acid sequences is shown in FIG. 1. As can be seen there, glutamic acid (E) is found at position 452 of the capsid protein in each of the exemplified VS-FCV isolates when optimally aligned with SEQ ID NO: 1. The FCV-Kaos capsid protein (SEQ ID NO: 3), however, has a deletion of one amino acid residue in position 442. When optimally aligned to SEQ ID NO: 1, glutamic acid (E) found in position 451 in the FCV-Kaos sequence corresponds to position 452 and is thus considered to be at position 452 for the purposes of this invention.

Optimal alignment is typically determined by visual inspection taking into account, for example, deletions and additions. A protein sequence may also be aligned with SEQ ID NO: 1 using the BLAST algorithm using default parameters. The BLAST algorithm is described in Altschul et al., *J. Mol. Biol.* 215:403-410 (1990). Software for performing BLAST analyses is publicly available through the National Center for Biotechnology Information (NCBI). For amino acid sequences, the BLASTP program uses as defaults a word length (W) of 3, an expectation (E) of 10, and the BLOSUM62 scoring matrix.

An "immunologically effective amount" refers to an amount of an immunogen sufficient to induce a detectable humoral or cellular immune response in an animal.

An "attenuated" virus refers to a virus that is either unable to colonize a host, unable to cause disease in a host or causes significantly reduced disease symptoms in a host. Attenuated viruses typically lack a genetic component involved in host colonization or pathogenicity.

A "protective immune response," as used herein, refers to a cellular or humoral immune response that prevents or delays infection or disease caused by a specified pathogen.

A "biological sample" refers to any sample obtained from a living or dead organism. Examples of biological samples include biological fluids and tissue specimens. Examples of tissue specimens include fetal brain tissue, spinal cord, and placenta. Examples of biological fluids include blood, serum, plasma, urine, ascites fluid, cerebrospinal fluid and fetal fluid.

A) Feline Virulent Systemic Calicivirus FCV-Kaos

The instant invention relates to novel virulent systemic feline calicivirus (VS-FCV) strains such as FCV-Kaos causing a highly contagious and fatal hemorrhagic fever syndrome. The virus strains causing outbreaks of VS-FCV are genetically distinct, but cause similar disease and vaccine resistance. The novel FCV-Kaos strain arises by spontaneous mutation from high density cat populations and then spreads readily to associated cats. In addition, FCV-Kaos is not neutralized by antibodies to the routine FCV vaccine strains (e.g., FCV-F9). Hence, vaccinated cats are not protected against this mutant strain. The mortality that is associated with this new strain is as high as 50% in effected animals. The source of the mutant strain is often kittens from shelters that are seen in private practices. The virus spreads quickly via contact (e.g., cat-to-cat, person-to-cat) to client owned animals. It is predicted that this virus may extend into the general population of cats (e.g., 70,000,000 pet cats in the U.S.), likely affecting hundreds of thousands of animals unless a vaccine is available to immunize the general cat population. Thus, it is an object of this invention to provide a vaccine that will induce broader immunity than so far available through current calicivirus vaccines to prevent viral infections by FCV-Kaos. FCV-Kaos has been deposited with the American Type Culture Collection under accession number PTA-5798.

One embodiment of the invention provides an immunogenic composition for immunization against a viral infection by FCV-Kaos, wherein the immunogenic composition comprises an immunologically effective amount of the virus and a physiological carrier. Optionally, the vaccine includes an adjuvant. The FCV-Kaos strain may be live, attenuated, or inactivated.

Symptoms of the FCV-Kaos strain include, but are not limited to, high fever (i.e., highly contagious and fatal hemorrhagic fever syndrome); facial and limb edema (e.g., swelling); ulceration (e.g., crusting and focal hair loss) especially on the face, muzzle and pinnae; icterus; pancreatitis; dyspnea; DIC (disseminated intravascular coagulation).; death in severe cases (death may occur in some cats with minimal preceding signs); hyperbilirubinemia; hyperglucosemia; increased CPK (creatinine phosphokinase); nasal and ocular discharge; oral ulceration; anorexia; and depression.

In particular, the mutant strain causes a hemorrhagic-like fever in cats. Cats develop this high fever, become depressed, often have oral and nasal discharge, and commonly develop swellings on their face, trunk, and lower extremities. Cats with milder signs sometimes recover within a few days, while cats with severe signs often die despite extensive symptomatic treatment. More specifically, cats present variably with approximately 50% having facial and paw edema; 90% being febrile (as high as 106 F.); 50% with classical signs of upper respiratory tract infection (URI)

such as ocular and nasal discharge, conjunctivitis, and vesicular or ulcerative stomatitis; 20% with icterus; and 30-40% with hemorrhage such as from nose and feces. Necropsy findings are also variable, including lung consolidation and pneumonia in 80% cats; hepatomegaly in 50% cats; pancreatitis in 10% cats; and pericarditis in 10% cats.

The incubation period for this strain in most cases is between 1-5 days. However, a few cases appear to have developed up to 12 days after the last known exposure. Cats of all ages, including fully vaccinated cats, are affected by this strain. A significant percentage of cats may continue to shed virus for some time after recovery from clinical signs, as is the case with other strains of feline calicivirus. Therefore, cats may still be infectious to others following early recovery.

FCV-Kaos, which is one example of a VS-FCV strain, may be present systemically, and may be shed in feces and in nasal, ocular and oral secretions. Transmission of FCV-Kaos occurs easily. Spread of disease is facilitated by client and technician traffic between hospitals. The virus can be very readily spread by fomites (i.e., any object that functions to transfer infection contaminated by pathogens from a diseased source) as well as direct transmission. It can be carried for at least several hours on contaminated hands, clothing, instruments, shoes, and the like. This virus may be carried home on clothing contaminated by handling infected cats, resulting in infection of cats that were never directly exposed to a sick cat (i.e., person-to-cat transmission). Droplet transmission is possible over as long as a distance as 1-2 meters. Although, FCV-Kaos may be carried through ventilation systems on dust and hair, airborne transmission over distances greater than a few feet is not normally associated with this strain. Recognition of the infectious nature of the disease may often be delayed because a case is not seen at the hospital where the disease first spreads, and subsequent spread to other hospitals occurs when owners take cats infected at one hospital to another hospital for treatment. Thus, careful attention to prevention of fomite transmission is important to prevent spread of FCV-Kaos. VS-FCV can persist in the environment in a dried state at room temperature (20° C.) for up to 28 days. This may play a role in the seemingly delayed transmission of infection.

VS-FCV strains, such as FCV-Ari and FCV-Kaos, arise most often from multiple cat environments such as shelters and catteries. Kittens borne to persistently infected mothers may shed virulent VS-FCV while showing minimal clinical signs themselves compared to adult cats. Hence, there may be a role for kittens in propagating VS-FCV. The high proportion of kittens, high population turnover and constant influx of vulnerable animals common to many shelters and rescue groups further increases the opportunity for high level virus replication, host switching, viral spread, replication and mutation. Generally, methods of spreading the disease have implications for VS-FCV control methods. In particular, mildly affected animals can play an important role in disease transmission (e.g., an apparently well cat is released home and his littermate shortly thereafter develops the fatal disease).

Cats of all ages are susceptible to FCV-Kaos, but adults are at significantly greater risk than kittens for severe disease and death. This is often the case when the reaction of the immune system is correlated with the severity of the disease. Vaccinated cats (e.g., FCV-F9) can be infected and suffer severe disease and death from FCV-Kaos, as is commonly the case. Strains of VS-FCV are generally vaccine resistant. Mutations that causes hemorrhagic strains of FCV may be linked to a change in antigenic structure that confers vaccine resistance. Viral culture, cDNA sequencing and serology of exposed cats allows for recognition of a wide range of clinical manifestations of VS-FCV disease, including mild and subclinical infections. Viral isolation from oropharyngeal swabs by culture and PCR proves to be a sensitive method of diagnosing disease when samples are obtained during acute infection or at necropsy. Positive cultures can be obtained even from asymptomatic cats soon after exposure. Since sensitivity of viral isolation decreases substantially later in the disease, a single negative swab cannot rule out low level excretion. Serology is useful to confirm a history of exposure, and is usually sensitive and specific based on any samples obtained during an outbreak.

Isolates of FCV-Kaos are closely related to one another, but are not closely related to FCV-Ari, another strain of VS-FCV which has been characterized by cDNA sequencing as described in Pedersen et al. *Vet. Microbiol.* (2000) 73:281-300. This may indicate that the mutation causing VS-FCV disease is different in each case. Because FCV is commonly isolated from the oral cavity of clinically healthy cats and cats with URI, positive viral culture or PCR from a cat with signs of vasculitis should not be considered diagnostic of VS-FCV disease without the support of cDNA sequencing demonstrating a distinct strain in more than one affected cat.

Some cats which survived FCV-Kaos infection may become chronic carriers, as commonly occurs with other strains of FCV. For example, cats infected with FCV-Ari are known to be culture positive up to 10 weeks after infection. Also, shedding of FCV-Kaos may persist at least 16 weeks in some cats. Hence, chronic carriers could pass VS-FCV strains to other cats long after recovery from clinical signs. Widespread susceptibility to FCV-Kaos infection exists regardless of age, health or vaccination status. Although, a highly virulent infection may kill off its hosts faster than disease can spread, in the outbreak documented herein (see Examples) at least 32 cats survived and some continued to shed virus indistinguishable from virulent FCV-Kaos. If the virus retains the same virulence and ease of spread that is observed early in an outbreak, it is likely that additional outbreaks would arise from this potential reservoir of infected cats. Mutation that lead to VS-FCV may revert during passage to yield a less or more virulent strain, and variant strains arise in persistently infected cats. Thus, FCV-Kaos infection poses a significant risk to the cat population and may lead to further serious outbreaks and spreading of disease.

B) Feline Virulent Systemic Calicivirus FCV-Ari

The instant invention also relates to a novel virulent systemic feline calicivirus (VS-FCV) strain such as FCV-Ari, an atypical and highly contagious FCV. FCV-Ari infection in cats manifests in its severest form by a systemic hemorrhagic-like fever that is similar to the one observed with FCV-Kaos infection. The new isolate, FCV-Ari, can be partially neutralized at negligible to low titer by antiserum against the universal FCV-F9 vaccine strain. Cats immunized with FCV-F9, and then challenge-exposed shortly thereafter with FCV-Ari, develop a slightly milder self-limiting form of the disease, indicating a low partial protection, compared to FCV-Kaos (supra). However, antibodies against the universal FCV-F9 vaccine strain do not significantly cross-react with FCV-Ari and immunization with FCV-F9 provides only a small measure of immunity for cats. A large proportion of previously vaccinated cats (i.e., immunized with parenteral FCV-F9 vaccine) die soon after exposure to FCV-Ari.

The disease caused by FCV-Ari appears to target blood vessels, as evidenced by the severe edema (sometimes hemorrhage) in subcutaneous tissues and lungs and local necrosis of skin and adipose tissues. Loss of vascular integrity relates to a significant drop in serum proteins, icteric serum (from breakdown of extravasated red blood cells), variable thrombocytopenia, and coagulopathies. There are also elevations in CPK that indicate myonecrosis. Generally, features of this disease include high mortality, the tendency to cause more severe disease in older animals, the ease of spread, the acute nature, hepatocyte tropism, and widespread vascular disease. It is noteworthy that the infection may persist in cats that are dying, i.e., the virus is still present in the blood of a cat at the time of death. FCV-Ari is a highly virulent strain that is most destructive to older animals. Although, inherent resistance factors may also play a role, in that, some cats develop milder self-limiting disease while others are devastated by infection. FCV-Ari, symptoms and disease are described in detail in Pedersen et al., *Vet. Microbiol.* (2000) 73:281-300 which is incorporated by reference herein. FCV-Ari has been deposited with the American Type Culture Collection under accession number PTA-5797.

One embodiment of the invention provides an immunogenic composition for immunization against a viral infection by FCV-Ari, wherein the immunogenic composition comprises an immunologically effective amount of the virus and a physiological carrier. Optionally, the vaccine includes an adjuvant. The FCV-Ari strain may be live, attenuated, or inactivated.

Another embodiment of the invention provides an immunogenic composition for immunization against a viral infection by VS-FCV, not including FCV-Ari, wherein the immunogenic composition comprises an immunologically effective amount of the virus and a physiological carrier. Optionally, the vaccine includes an adjuvant. The FCV-Ari strain may be live, attenuated, or inactivated.

C) Imunogenic Compositions

One aspect of the invention provides for a method of immunizing a cat against VS-FCV strains such as FCV-Kaos, FCV-Ari, or FCV-Bellingham which comprises administering to the cat an effective dose of an immunogenic composition of the invention. In a preferred embodiment of the invention, attenuated or killed FCV-Kaos virus is combined or mixed with various solutions and other compounds as are known in the art. In another preferred embodiment of the invention, attenuated or killed FCV-Ari virus is combined or mixed with various solutions and other compounds as are known in the art. In yet another preferred embodiment of the invention, attenuated or killed FCV-Bellingham virus is combined or mixed with various solutions and other compounds as are known in the art. Immunogenic compositions may be prepared as injectables, as liquid solutions or emulsions. The viral strains of the invention may be mixed with pharmaceutically-acceptable excipients. Excipients may include water, saline, dextrose, glycerol, ethanol, and combinations thereof. The vaccine may further contain auxiliary substances such as wetting or emulsifying agents, pH buffering agents, or adjuvants to enhance the effectiveness of the vaccines.

Immunogenic compositions of the present invention may comprise the whole virus and/or virally-infected cell lines. The virus may be wholly or partially inactivated and utilized as an immunogen in the composition. Partial inactivation may be achieved by passage at elevated temperatures or by contact with mutagens, such as ultraviolet light, ethyl methanesulfonate, and the like. Complete inactivation may be achieved by contact with other agents, including formalin, paraformaldehyde, phenol, alpha-lactopropionate, ultraviolet light, heat, psorlens, platinum complexes, ozone and other viricidal agents.

In addition to whole virus, viral proteins or peptides may also be used in the preparation of subunit vaccines prepared by known techniques. Those of skill will readily recognize that it is only necessary to expose a mammal to appropriate epitopes in order to elicit effective immunoprotection. The epitopes are typically segments of the whole protein. Thus, it is possible to prepare immunogenic compositions of the invention comprising isolated proteins or polypeptides as immunogens in place of the attenuated or killed whole virus. One of skill will recognize that such immunogens can be prepared using recombinant techniques. It is also routine to alter a natural protein's primary structure to create derivatives embracing epitopes that are identical to or substantially the same as (immunologically equivalent) the naturally occurring epitopes. Such derivatives may include peptide fragments, amino acid substitutions, amino acid deletions and amino acid additions within the natural amino acid sequence for the select target protein. For example, it is known in the protein art that certain amino acid residues can be substituted with amino acids of similar size and polarity without an undue effect upon the biological activity of the protein.

Polypeptides displaying antigenic regions capable of eliciting protective immune response are selected and incorporated in an appropriate carrier. Alternatively, an immunogenic portion of a viral protein or proteins may be incorporated into a larger protein by expression of fused proteins. The preparation of subunit vaccines for other viruses is well known and is described in various references, including Lerner et al. (1981) *Proc. Natl. Acad. Sci. USA* 78:3403 and Bhatanagar et al. (1982) *Proc. Natl. Acad. Sci. USA* 79:4400. See also, U.S. Pat. No. 4,565,697 (where a naturally-derived viral protein is incorporated into a vaccine composition); U.S. Pat. Nos. 4,528,217 and 4,575,495 (where synthetic peptides forming a portion of a viral protein are incorporated into a vaccine composition). Other methods for forming vaccines employing only a portion of the viral proteins are described in U.S. Pat. Nos. 4,552,757; 4,552,758; and 4,593,002.

The vaccines prepared as described above may be administered in any conventional manner, including oronasally, subcutaneously, intraperitoneally or intramuscularly, except that oronasal administration will usually not be employed with a partially inactivated virus vaccine. Adjuvants will also find use with subcutaneous and intramuscular injection of completely inactivated vaccines to enhance the immune response. The preparation of viral vaccine compositions optionally employing adjuvants is described in numerous standard references, such as Remington's Pharmaceutical Sciences, Mack Publishing Co., Easton, Pa., 16th ed., 1982.

The dosage form and immunogen content of the compositions of the invention will vary depending on the nature of the immunogen (i.e., whole virus, infected cell, or subunit) and the route of administration. Usually, a single dose will have a total volume including carrier, adjuvant, and any other components, in the range from about 0.1 ml to about 5 ml, more usually being from about 0.5 ml, more usually being from about 0.5 ml to about 3 ml. The amount of inactivated or attenuated whole virus in each dose will usually be in the range from about 0.1 mg to about 5 mg, usually being from about 0.2 mg to 2 mg. (For inactivated virally-infected cell lines, each dose may typically contain from about 10.sup.6 to 10.sup.8 cells, usually about 5.times.10.sup.6 to 5.times. 10.sup.7 cells.)

The number and timing of the inoculations will be sufficient to elicit the desired immunoprotective response against subsequent challenge by VS-FCV (e.g., FCV-Kaos, FCV-Ari, FCV-Bellingham). Usually, there will be at least two inoculations spaced at least one week apart, more usually being from two to 10 inoculations spaced over a period from two to thirty weeks. Often, a final inoculation may be administered at some longer interval following an initial series of administrations. The selection of optimum administration patterns for a particular vaccine formulation is well within the skill in the art.

The compositions of the invention can be formulated for oronasal delivery. Formulations suitable for nasal administration, wherein the carrier is a solid, include a coarse powder having a particle size, for example, in the range of about 10 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the active ingredient. Various ways of such administration are known in the art. The pharmaceutical formulation for nasal administration may be prepared as solutions in saline, employing benzyl alcohol or other suitable preservatives, absorption promoters to enhance bioavailability, fluorocarbons, and/or other solubilizing or dispersing agents known in the art. The unit dosage for nasal administration can be from 1 to 3000 mg, e.g., 10 to 1000 mg, or 1 to 10 mg of active ingredient per unit dosage form.

Vaccines of the invention may be combined with other vaccines for the same or other diseases to produce multivalent vaccines. A pharmaceutically effective amount of the immunogen can be employed with a pharmaceutically acceptable carrier such as a protein or diluent useful for the vaccination of mammals, particularly cats. Other vaccines may be prepared according to methods well-known to those skilled in the art.

Examples of other vaccines, including other cat vaccines, that can be combined with attenuated or killed FCV Kaos or FCV-Ari include, but are not limited to, panleukopenia virus antigens, feline herpesvirus I antigens, leukemia virus antigens, and rabies antigens.

D) Assays for Detecting VS-FCV

The VS-FCV virus strains of the instant invention (e.g., FCV-Kaos, FCV-Ari, FCV-Bellingham) and antibodies that specifically bind to them can be detected and/or quantified using any of a number of well recognized immunological binding assays. For a review of the general immunoassays, see also Methods in Cell Biology: Antibodies in Cell Biology, volume 37 (Asai, ed. 1993); Basic and Clinical Immunology (Stites & Terr, eds., 7th ed. 1991). Immunological binding assays (or immunoassays) typically use an antibody that specifically binds to a protein or antigen of choice. The antibody may be produced by any of a number of means well known to those of skill in the art and as described above. Alternatively, a protein or antigen of choice may be used to bind antibodies in the serum of an infected animal. The protein or antigen may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled antigen or a labeled antibody. Alternatively, the labeling agent may be a third moiety, such a secondary antibody, which specifically binds to the antibody/antigen complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., J. Immunol. 111:1401-1406 (1973); Akerstrom et al., J. Immunol. 135:2589-2542 (1985)). The labeling agent can be modified with a detectable moiety, such as biotin, to which another molecule can specifically bind, such as streptavidin. The streptavidin may be bound to a label or detectable group as discussed below. A variety of detectable moieties are well known to those skilled in the art.

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^{3}H$, $^{125}I$, $^{35}S$, $^{4}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

A number of assay formats are well known. The assays can be either competitive or non-competitive assays. Typical assays will be carried out in the ELISA format. Western blot (immunoblot) analysis can be used to detect and quantify the presence of the viral antigens in a sample. Other assay formats include liposome immunoassays (LIA), which use liposomes designed to bind specific molecules (e.g., antibodies) and release encapsulated reagents or markers. The released chemicals are then detected according to standard techniques (see, Monroe et al., Amer. *Clin. Prod. Rev.* 5:34-41 (1986)).

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Nucleic acid-based assays can also be used to detect the presence of VS-FCV-Kaos DNA and RNA in a sample. Such assays include numerous techniques known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis.

E) EXAMPLES

The following specific examples are intended to illustrate the invention and should not be construed as limiting the scope of the claims.

Example 1

Data Collection

An outbreak of FCV-Kaos occurred among cats at three veterinary practices in the area of Los Angeles, Calif. during June and July of 2002. A hemorrhagic fever like syndrome was observed, with affected cats showing signs of vasculitis, facial and limb edema, and multiple organ involvement in addition to more commonly observed signs of caliciviral respiratory infection. A total of 54 cases were documented. Overall mortality was 40%, and mortality in adult cats (>6 months) was 59%. Adult cats were more likely than kittens to suffer severe disease or death (odds ratio 9.56, CI= 2.82 –32.39, p<0.001). The attack proportion was 94%. 21% of cases were mild or subclinical. Many affected cats had been vaccinated against feline calicivirus, however, antibodies to the vaccine strain FCV-F9 did not neutralize FCV-Kaos. In fact, at least twenty-six (48%) of the affected cats had a history of vaccination against feline herpes virus, calicivirus, and panleukopenia virus. Spread of FCV-Kaos occurred readily within and among hospitals and homes via fomites and movement of infected cats. Examples 1-8 (vide infra) provide a detailed description of FCV-Kaos outbreak, -symptoms, -illness, -pathology, and -analysis. Example 9 (vide infra) describes the earlier outbreak of a similarly virulent and highly contagious strain, FCV-Ari.

The information on FCV-Kaos cases was collected by interviews conducted in-person and by phone, and by examination of medical records. Three veterinary practices and one rescue group were affected by the FCV-Kaos strain. Each affected practice was visited and all available records of suspect cases were reviewed. The information was collected on all cats hospitalized as inpatients during the outbreak, whether or not they showed signs of infection. A written summary of all kittens present within the rescue group's foster home network at the time of the outbreak was provided by rescue group personnel.

Example 2

Case Definition

The FCV-Kaos cases were classified as confirmed -, suspect -, or possible.

A "confirmed" case was defined as any of the following:

(a) A cat from which FCV-Kaos was isolated and genetically sequenced.

(b) A cat exposed to a case confirmed by genetic sequencing which exhibited either sudden death or edema of the face or feet not explained by other causes, and with one or more additional signs of caliciviral infection (e.g., fever, oral ulcers, ocular or nasal discharge, limping).

A "suspect" case was defined as any of the following:

(a) A cat exposed to a confirmed case, in which sudden death or edema or sores/alopecialulceration of the face or feet with other signs of caliciviral infection was reported but not confirmed by a veterinarian or for which other causes were not ruled out.

(b) A cat exposed to a confirmed case and seropositive to FCV-Kaos but with no abnormal clinical signs reported.

A "possible" case was defined as follows:

A cat exposed to a confirmed case and reportedly febrile, with other signs of upper respiratory infection (e.g., oral ulcers, ocular or nasal discharge, anorexia) but without edema or death and for which no viral culture or serology was available.

Example 3

Clinical Signs and Pathology

Fever was the most commonly reported clinical symptom in cats, affecting 44/54 animals (81%). Median temperature was 40.6° C. (105.1° F.) with a range from 39.4° C. to 42.4° C. (103.0° F. to 106.5° F.). Either limb and/or facial edema was reported in 28/54 (52%) of cases (limb edema was reported in 25 cases; and facial edema in 14 cases). In decreasing order of frequency, other abnormalities reported were: oral ulcers (25/54, 46%); nasal discharge (16/54, 30%); dyspnea (9/54, 17%); sores, crusting or alopecia of the face, pinnae, or feet (9/54, 17%); ocular discharge/conjunctivitis (6/54, 11%); clinically apparent jaundice (6/54, 11%); pleural effusion (5/54, 9%); diarrhea (4/54, 7%); vomiting (4/54, 7%); and limping (3/54, 6%). The hemorrhagic fever included signs that were characteristic of vasculitis and frank hemorrhage. Frank hemorrhage was observed in two cases (from the nose in one case, and from the nose and rectum in another case).

Severity of illness ranged from no signs at all to fatal illness. No abnormalities were observed in 3/54 cases (6%) that were considered to be infected (based on positive viral culture and sequencing). In 8/54 cases (15%), only mild signs were observed, limited to oral ulcers, nasal/ocular discharge and fever <104° F. Moderate signs were reported in 8/54 cases (11%), including fever >104° F., lethargy/inappetance for >1 day, sores/crusting/pustules of skin, with ocular/nasal discharge and/or oral ulcers. Severe signs including edema, respiratory distress and/or death were reported in 35/54 (65%) cases; 13 of the 35 cats with severe signs survived.

The date of first exposure was determined in 17 cases. For these cases, the median time from exposure to first observation of signs was 4 days, with a range of 1 to 12 days. The longer apparent incubation times occurred in cats secondarily exposed by another sick cat in the home. In cats exposed as inpatients, the longest time observed between exposure and observation of signs was 5 days. One cat developed signs up to 34 days after his first probable exposure. He may have been exposed a second time between 2-15 days prior to the onset of symptoms.

Blood chemistry panels were available for 10 cases. Abnormal findings on blood chemistry included hyperbilrubinemia in 6/10 cases (range 0.6-3.9 mg/dl, reference range=0.1-0.4 mg/dl); hypoalbuminemia in 5/10 cases (range 1.1-2.1 g/dl, reference range 2.5-3.9 g/dl); elevated aspartate aminotransferate (AST) in 3/10 cases (range 103-223 IU/L, reference range 10-100 IU/L); mildly elevated alanine aminotransferase (ALT) in 2/10 cases (range 102-116 IU/L, reference range 10-100 IU/L); and elevated creatine phosphokinase (CPK) in 5/10 cases (range 639-10930 IU/L, reference range 56-529 IU/L).

Complete blood counts were available for 8 cases. 3/8 cases had a mild neutrophilia (range 8549-11616 cells/µl, reference range 2500-8500 cells/µl), and 5/8 had a mild to moderate lymphopenia (range 180-1188 cells/µl, reference range 1200-8000 cells/µl). Hematocrit was slightly decreased in 2/8 cases (25%, reference range 29-48%).

Gross necropsy results were available for five cats. In all cats there was abundant bright yellow subcutaneous edema most markedly affecting the face and limbs. In two cats dependent edema extended along the thoracic wall and affected the entire inguinal and axial regions. Conjunctiva were red and swollen with crusted material adhered to the medial canthi. Ulcers were present on all cats although sites and extent were variable. Three cats had circumferential ulceration at the junction between the paw pads and haired skin. In two cats there were 0.4 cm diameter to coalescing ulcers of the dorsal, lateral and ventral tongue surfaces. In two cases, although the tongue appeared unaffected there was ulceration of the septum of the nares and of the haired skin overlying the nose. In all cats there was up to 100 ml of pale red, slightly opaque fluid within the abdominal and thoracic cavities and in one cat there was extensive pericardial fluid of similar character. In two cases, there was minimal and multifocal omental fat necrosis. Histologic analysis revealed that the ulcerations in all cases corresponded to microscopic vast regions of epithelial necrosis and ulceration with minimal inflammation. The superficial dermis underlying this region was often disrupted and expanded by edema and cell debris. The remainder of the dermis was minimally affected excepting occasional extension of necrosis into follicular epithelium. In three cats massive or centrilobular, peracute hepatic necrosis was present.

Example 4

Serology

Serum was collected from 19 cats that had survived infection with FCV-Kaos, and from 2 kittens that may have been indirectly exposed but were presumably uninfected (based on absence of clinical signs and negative viral culture). Serum samples were collected 1-6 weeks after the estimated time of infection or exposure. Virus neutralizing titers were determined by reacting four-fold serial dilutions of serum with a constant amount of virus. The dilutions of serum used were 1:4, 1:16, 1:64, 1:256, 1:1024, 1:4096, and 1:16,384. Crandell feline kidney cells (CrFK) were used in 96-well plates for the titration.

50 µl of patient serum was diluted serial four fold (1:4 to 1:16,384, supra) with tissue culture medium in 96 well culture plates. 50 µl of tissue culture medium containing approximately $1000TCID_{50}$ (1000 tissue culture infectious dose) of FCV was then added to each well and incubated for 1-2 hours at 37° C. The serum/virus mixture from each well was then transferred into corresponding wells of a culture plate containing 1-2 day old, just confluent, CrFK cells. Each serum was tested against three virus isolates: FCV-F9 (vaccine strain), FCV-Kaos, and FCV-case 53 (an unrelated field isolate from case 53). The plates were incubated for 24 hours and observed under an inverted microscope for typical FCV CPE (cytopathic effect). The last well containing any detectable CPE was read as endpoint. A CPE at a dilution of 1:16 or greater was considered a positive result.

Results of serology are shown in Table 1 below. All cats with either confirmed FCV-Kaos infection or housed in the same cage as an FCV-Kaos positive cat were seropositive to FCV-Kaos. All cats housed in the same cage as case 53 were seropositive to FCV-53, as were two cats in group 6 with no known history of exposure to case 53. The cats in group 2 were not directly exposed to case 53 or FCV-Kaos. These cats never showed clinical signs of infection, were culture negative for FCV infection, and were seronegative for both viral strains. There was no evidence of cross-reaction between FCV-F9 and either FCV-Kaos or FCV-53 (virus neutralizing antibody levels <1:4).

TABLE 1

| | | | | Antibody Titer to FCV Strain | | |
|---|---|---|---|---|---|---|
| Case # | Group[1] | Vaccine Status | Severity | FCV-case53[2] | Vaccine (FCV-F9) | FCV-Kaos | FCV Strain Isolated |
| 53 | 1 | Yes | 3 | 1:16 | 1:16 | 1:16 | FCV-case53, FCV-Kaos[3] |
| 41 | 1 | no | 4 | 1:256 | 1:16 | 1:256 | FCV-Kaos |
| 54 | 1 | no | 2 | 1:256 | 1:16 | 1:64 | FCV-Jengo[4] |
| 52 | 1 | Yes | 3 | 1:64 | 1:64 | 1:16 | None[5] |
| 51 | 1 | Yes | 2 | 1:256 | 1:16 | 1:64 | None |
| 40 | 1 | Unknown | 3 | 1:256 | 1:16 | 1:16 | None |
| 50 | 1 | Yes | 2 | 1:1024 | 1:16 | 1:64 | None |
| R1[6] | 2 | Yes | 0 | 1:4 | 1:64 | <1:4 | None |
| R2[6] | 2 | Yes | 0 | <1:4 | 1:4 | <1:4 | None |
| 32 | 3 | Yes | 2 | <1:4 | 1:4 | 1:256 | None |
| 33 | 3 | Yes | 1 | 1:4 | 1:4 | 1:64 | FCV-Kaos |
| 31 | 4 | yes | 3 | <1:4 | 1:16 | 1:64 | None |
| 35 | 5 | Yes | 4 | <1:4 | 1:64 | 1:256 | FCV-Kaos |
| 36 | 5 | Yes | 4 | 1:4 | 1:16 | 1:1024 | FCV-PM |

TABLE 1-continued

| | | | | Antibody Titer to FCV Strain | | | |
|---|---|---|---|---|---|---|---|
| Case # | Group[1] | Vaccine Status | FCV- Severity | FCV- case53[2] | Vaccine (FCV-F9) | FCV-Kaos | FCV Strain Isolated |
| 34 | 5 | Yes | 4 | <1:4 | 1:16 | 1:256 | None |
| 12 | 6 | Yes | 4 | 1:4 | 1:16 | 1:64 | None |
| 18 | 6 | Yes | 4 | 1:4 | 1:4 | 1:64 | FCV-Kaos |
| 9 | 6 | Yes | 4 | 1:4 | 1:64 | 1:256 | None |
| 10 | 6 | Unknown | 4 | 1:4 | 1:4 | 1:256 | FCV-Kaos |
| 11 | 6 | Yes | 4 | 1:16 | 1:64 | 1:256 | None |
| 21 | 6 | Unknown | 4 | 1:64 | 1:16 | 1:256 | FCV-Kaos |

[1]Groups 1-5 were kittens from the rescue group. Each group was housed in a separate cage, but all were in the same general area and cared for by the same caretakers. Group 6 cats were from a practice; the cats were housed in isolation in separate cages.
[2]Field strain of calicivirus isolated from one rescue kitten during outbreak and associated with mild URI signs.
[3]FCV-case53 isolated before exposure to case 41; FCV-Kaos isolated after exposure to case 41.
[4]Field strain of calicivirus isolated from 2 rescue kittens during outbreak, wherein both kittens had signs of severe liver disease.
[5]No FCV isolated on 2-5 attempts over 10 week follow up period.
[6]R1 and R2 were never symptomatic or culture positive for calicivirus infection, and were therefore not considered cases.

Example 5

Histology

All tissue samples were fixed in 10% neutral buffered formol-saline. Selected tissues were embedded in paraffin, sectioned at 4 µm, and mounted on positive-charged glass slides (Superfrost/plus, Fischer Scientific, Pittsburgh, Pa.). Tissue sections were stained with hematoxylin and eosin (HE) for routine light microscopy examination.

Example 6

Viral Isolation, Culture, and Sequencing 77 cultures were provided. 19/77 cultures were from cats sampled once, and 18/77 were from cats sampled 2-5 times at 1-3 week intervals. Viral isolation performed at the peak of clinical signs was positive in 88% (15/17) of cases. In some of the cats sampled repeatedly, intermittent and persistent shedding was observed.

Caliciviruses were isolated from cat serum and cultured on a confluent monolayer of Crandell feline kidney cells (CrFK) from freshly harvested spleen or lung, EDTA-anticoagulated whole blood, nasal discharge, or oropharyngeal secretions collected on sterile cotton swabs and transported in sterile saline solution or in sterile saline with the addition of 0.02 mg/ml of penicillin and amikacin. Cells were maintained at 37° C. in air with 5% $CO_2$ and growth media containing one half Liebovitz L-15 media and one half MEM (Eagle's minimum essential media). The media contained 10% FBS (fetal bovine serum), 100 U penicillin G/ml, and 100 µg streptomycin/ml of media. A viral infection was confirmed by the presence of a characteristic cytopathic effect (CPE) within cells from 12-52 hours. After inoculation, tissue culture fluid was harvested from all infected cells and total RNA was extracted using a kit (Qiagen Tissue Kit, Chatsworth, Mass.). Reverse-transcription/nested-polymerase chain reaction was performed as described in Pedersen, et al, Vet Microbiol 73(4):281-300 (2000). All apparently culture-positive isolates were PCR-positive. Fragments were purified by Microcon-50 Columns (Millipore Corp, Bedford, Mass.) and all positive results were confirmed by sequencing, i.e., by automated cDNA sequencing using a sequencing service (Davis Sequencing, Davis, Calif.). Thus, FCV-Kaos was isolated and confirmed by cDNA sequencing. In fact, all positive results were confirmed by cDNA sequencing.

Example 7

Viral Characterization

Viral isolates from symptomatic and exposed cats were sequenced and compared to several field strains of FCV, vaccine strain (FCV-F9), and FCV-Ari (a VS-FCV strain isolated in a 1998 Northern California outbreak as described in Pedersen et al., Vet Microbiol 73:281-300 (2000) (supra). All isolates of FCV-Kaos clustered within a single clade, being genetically distinct from the other strains used for comparison. Isolates of FCV-Kaos were characterized by a three base pair deletion not observed in the other strains.

Example 8

Statistical Analysis of Infected Cats

The data summary was performed in "R" (The R-Development Core Team) which is a language and environment for statistical computing and graphics similar to the S language and environment which was developed at Bell Laboratories (formerly AT&T, now Lucent Technologies). R can be considered as a different implementation of S. There are some important differences, but much of the code written for S runs unaltered under R (Richard A. Becker, John M. Chambers, and Allan R. Wilks. The New S Language. Chapman & Hall, London, 1988). Possible associations of cases with age, vaccination status and sex were evaluated by chi-square contingency tests. Univariate evaluation of possible risk factors was performed by calculating odds ratios and confidence intervals (function "odds" on R). Values of $P<0.05$ were considered significant.

The attack proportion for cats either hospitalized concurrently with a case cat for $\geq 12$ hours or from the same household as a case cat was 94% (47/50). The case fatality proportion overall was 41% (22/54). In cats >1 year old, the case fatality proportion was 59% (19/32), and in kittens <6 months old it was 14% (3/22). Adult cats (>1 year old) had significantly higher odds than kittens (<6 months old) for severe disease or death (odds ratio 9.56, CI=2.82, 32.39, p<0.001). Sex was not a significant risk factor for severe disease or death. Few of the cats were known to be unvaccinated; therefore risk associated with vaccination could not be assessed in adult cats. Of the kittens whose vaccine status was known, 7 had received a modified live intranasal vaccine and 11 had received a modified live subcutaneous vaccine. There was no significant difference in likelihood or severity of disease between these two groups of vaccinated kittens.

Example 9

FCV-Ari

In 1998, another outbreak of a highly virulent, vaccine-resistant strain of VS-FCV, FCV-Ari, associated with a hemorrhagic-like-fever, was reported in Northern California as described in Pedersen et al., Vet Microbiol 73:281-300 (2000) (supra). Death occurred in 33-50% of FCV-Ari infected cats, and this strain proved highly contagious, spreading via contaminated fomites in spite of hygienic precautions in veterinary hospitals and research colonies. Distinctive clinical signs included facial and limb edema in febrile cats, and sudden death in some cases with few preceding signs. Since the report of the 1998 outbreak, at least four focal outbreaks of hemorrhagic fever like FCV have been recognized in Pennsylvania, Massachusetts, Tennessee and Nevada.

Example 10

Epidemiological Patterns

Clinical cases of VS-FCV infection were isolated incidents or clustered in epidemics characterized by rapid onset and spread, with enigmatic, gradual or abrupt conclusion. Cases were classified as confirmed, suspect, or possible. A confirmed case was defined as a cat with a consistent exposure history (i.e., from an affected practice or with contact with a confirmed case) from which a FCV strain was recovered with identical capsid hypervariable region sequences with a known case strain in the same epidemic. A suspect case was defined as a cat that had been exposed to a confirmed case and within two weeks developed clinical signs of VS-FCV infection, or a cat that had been exposed to a confirmed case and died suddenly within two weeks, or a cat that had been exposed to a confirmed case and was seropositive for seroconverted, regardless of whether the cat did or did not have clinical abnormalities. A possible case was defined by exposure to a confirmed case with development of fever or upper respiratory tract infection (URI) for which viral culture and serologic testing were not available.

The first recognition of the new syndrome was during a large focal epidemic involving six cats in northern California, from which a vaccine-resistant strain of FCV, designated FCV-Ari, was consistently recovered. Only cats exposed in one clinic were involved and the epidemic stopped abruptly. Subsequent, small outbreaks have been recognized in Pennsylvania, Massachusetts, Tennessee and Nevada. In summer, 2002, an outbreak of 54 cases occurred among three veterinary practices in the area of Los Angeles. An investigation of this outbreak was performed prospectively, and the inclusion of serological, molecular, clinical, and pathologic information yielded valuable insight into the epidemiology of this novel pathogen. VS-FCV spread rapidly in the outbreak in Los Angeles and infected virtually all cats in contact with case cats. The first four cases were hospitalized for routine care and developed fever and upper respiratory tract infections (URI) plus edema and crusting of the pinnae. All four cats recovered and were not followed up. One week later, a cat at an adjacent hospital developed peracute VS-FCV infection with fever and fatal cardiopulmonary arrest. Over the next week, the epidemic rapidly emerged to include 14 cats in these two practices and two cats at the home of a veterinary technician. Within 8 weeks, at least 54 cats had been infected of which 22 died, including many mature cats that had previously been completely healthy. The attack proportion for cats either hospitalized concurrently with a case cat for more than 12 hours or from the same household as a case cat was 94% (47/50). The median time from exposure to first clinical signs was four days (range 1-12 days). Longer incubation times occurred in cats secondarily exposed by another sick cat in the home. For example, one cat became ill 34 days after the first exposure and 2-15 days after a second exposure. In cats exposed as inpatients, the longest time observed between exposure and observation of signs was 5 days Viral isolation performed at the peak of clinical signs was positive in 88% of cases. (FCV culture was performed using EDTA-anticoagulated blood, oropharyngeal secretion, or spleen and lung specimens collected at the time of necropsy. Specimens were cultured on a confluent monolayer of Crandall feline kidney cells at 37° C. in air with 5% $CO_2$ in 1:1 Liebovitz L-15 medium and Eagle's minimum essential medium with 10% fetal bovine serum, 100 U of penicillin G/mL, and 100 µg of streptomycin/mL. Infection was confirmed by the presence of characteristic cytopathic effects within 12 to 52 hours.) In some of the cats sampled repeatedly, intermittent and persistent shedding was observed. The incubation period in field strains of respiratory FCV is only 1-2 days and virus shedding occurs two days to months after infection from ocular and nasal discharge, saliva, and feces of cats with and without clinical signs of infection. Routes of viral spread in the VS-FCV epidemic included direct cat-to-cat transmission, fomite transmission between clinics and to homes via technicians and owners, and transmission to outpatients via an asymptomatic carrier inpatient. Transmission declined after contaminated areas were thoroughly cleaned with sodium hypochlorite solution. Calicivirus can persist in the environment in a dried state at room temperature for several weeks and the calicivirus that causes rabbit hemorrhagic disease (RHDV) remained infective on cloth at room temperature for 105 days.

Although the overall mortality in the Los Angeles epidemic was 40, significantly higher mortality (59%) was observed in cats more than 6 months old, with only 14% mortality in kittens less than 6 months old (odds ratio 9.56, CI=2.82-32.39, P<0.001). 48% of the affected cats had been vaccinated against feline herpesvirus, FCV, and panleukopenia virus (seven cats with modified live intranasal high antigen mass vaccine and eleven cats with modified live subcutaneous vaccine). Whether or not vaccination increased disease risk, it was not protective. Gender was not a significant risk factor for severe disease or death. The total duration of the epidemic was six weeks.

Example 11

Pathogenesis

VS-FCV infection was distinctive in its clinical severity, tropism for epithelial cells, multisystemic attack, induction of systemic vascular compromise, and rate of involvement of visceral organs including lungs, pancreas, and liver. Seven cats from two VS-FCV outbreaks were evaluated pathologically in extensive detail. All seven cats had subcutaneous edema and ulceration of the oral cavity, with variable ulceration of the pinnae, paw pads, nares, and skin. Other lesions that were present in some affected cats included bronchointerstitial pneumonia, and pancreatic, hepatic and splenic necrosis. The extent and site of ulcers varied markedly, most frequently and severely affecting the dorsum of the tongue, with numerous smaller ulcers on the hard palate and gingiva. Lesions on feet ranged from circumferential hyperemia at the haired/non-haired junction to sloughing of footpads. Ulcers variably occurred in the nose, on pinnae and on haired skin. All cats had marked subcutaneous edema of the face and limbs. Histopathologically, lesions represented were epithelial necrosis and ulceration, with segmental epithelial necrosis of the stratum basale, stratum spinosum, and follicles early in haired skin, to full-thickness epithelial necrosis with ballooning degeneration in superficial layers and loss of distinct epithelial-subepithelial margin in more chronic lesions. Paw pad lesions were most severe at the junction between haired and non-haired skin.

All cats had pulmonary edema, four cats with blood tinged pleural effusion and another four with bronchointerstitial pneumonia. Acute lung lesions revealed circulating leukocytosis, regional alveolar edema, and few necrotic epithelial cells in alveolar spaces. In severe lesions, the alveolar interstitium was expanded by type II pneumocyte hyperplasia, accumulation of leukocytes in alveolar capillaries, and microthrombi. Alveoli were variably filled with foamy histiocytes, cell debris, fibrin and red blood cells. Many affected cats also had signs of liver or pancreatic involvement with hyperbilirubinemia, hypoalbuminemia, and elevated AST and creatine kinase. There were multiple small, discrete foci of peripancreatic and omental fat necrosis in three cats. In cats with liver involvement there was diffuse individualization of hepatocytes to extensive disruption of hepatocellular plates with cell to centrilobular necrosis. Inflammation was limited to small clusters of intrasinusoidal neutrophils adjacent to necrotic foci. Four of the seven cats had multifocal, peracute, pancreatic necrosis with saponification of adjacent fat. One cat each had massive splenic and lymphoid necrosis.

Immunohistochemical staining with a monoclonal antibody to FCV and transmission electron microscopy documented viral antigen within endothelial and epithelial cells in affected skin, nasal mucosa, tongue, buccal mucosa, pinna, and paw pads (all formalin fixed, paraffin-embedded tissues were immunohistochemically stained using the monoclonal antibody anti-feline calicivirus CV8-1A (c) provided by Custom Monoclonals Inc., Sacramento, Calif.). The staining intensity was proportional to the severity of the lesion, from the stratum basale and spinosum in early lesions to all layers of epithelium with chronicity. Virus was present in endothelial cells in small vessels throughout the submucosa, in exocrine pancreatic cells associated with regions of necrosis, in alveolar septae of lungs, and in lining cells of small bronchioles in chronic lesions of bronchointerstitial pneumonia. Using electron microscopy, virus was detected in paw pad epithelial cells, with mature virions within epithelial nuclei.

VS-FCV induced disease can manifest as fever, edema, multiple-organ failure, hemorrhage, shock and death. The increased risk of severe disease in older and/or vaccination cats suggested an immune-mediated component in addition to possible direct cellular damage induced by the virus. Inflammatory cells were not appreciated in the acute lesions regardless of severity. Adaptive immune responses could have contributed to disease severity, e.g., by antibody-dependent enhancement. Although disease progression was too rapid to involve a primary adaptive response, vaccinated cats would have had anemnestic immune responses, as would have many of the unvaccinated cats given the widespread exposure to field strain FCV. This age-related risk factor for disease severity was similar to that in rabbit hemorrhagic disease (RHD), where young rabbits experience self-limiting diseases while older infected rabbits experience almost 100% mortality.

An evaluation of cytokines (infra) in skin samples of cats with VS-FCV infection was performed to understand contributory roles of cytokines and indirectly some possible cellular effectors of injury and disease (. There was a statistically significant increase in TNF-α in affected tissues compared to controls (P=0.05). Affected tissues had, on average, 3.8 elevated cytokines while controls had only 1.4 (P=0.041), with prominent upregulation particularly in IL-10, TNF-α, and MIP-1α.

MIP-1α is a chemokine in the conserved C—C family, secreted by numerous cell types. It is chemoattractant primarily for macrophages and monocytes, pyrogenic and a potentiator of IFN-γ production. IL-10 is secreted by $T_H2$ CD4$^+$cells, CD8$^+$ cells, and macrophages, although it feeds back and inhibits further macrophage cytokine release. In the skin, IL-10 stimulates mast cells and IgA-producing B-cells, and upregulates MHC-II expression. TNF-α is a $T_H1$ cytokine from macrophages, lymphocytes, and others and may have been very important in the pathogenesis of VS-FCV by virtue of its ability to increase vascular permeability, stimulate acute phase responses from liver, and induce complement activation, fever, and shock. These changes with microthrombi, disseminated intravascular coagulation, and ultimately death were initiated by viral invasion of endothelium and epithelium, in contrast to some agents of systemic vascular compromise which are associated with inflammatory vasculitis, bacterial endotoxin, and activation of the kallikrein-kinin system as in RMSF, vasculitis due to immune complex deposition as in feline infectious peritonitis, or direct viral tissue cytotoxicity and monocyte invasion as in rabbit hemorrhagic disease (RHD).

Cytokines including IL-1β, IL-2, IL-4, IL-6, IL-10, IL-12p40, IL-18, IFN-γ, IFN-α, TNF-α, MIP-1α, and RANTES were evaluated by TaqMan PCR of cDNA as described in Foley et al. (Foley, J., C. Rand, and C. Leutenegger; in press; Inflammation and changes in cytokine levels in neurological feline infectious peritonitis; *Journal of Feline Medicine and Surgery*) with modifications. Formalin-fixed skin tissue corresponding to areas with light microscopic VS-FCV lesions or unaffected controls was steriley excised from paraffin blocks, deparaffinated with xylene; RNA was extracted using a kit (Qiagen Tissue Kit, Valencia, Calif.) and reverse transcribed with random hexadeoxyribonucleotide (pd(N)$_6$) primers (random hexamer; Promega, Madison, Wis.) and SuperScript II reverse transcriptase (Gibco BRL, Life Technologies, Grand Island, N.Y.). PCR was performed in a thermocycler/fluorometer (ABI Prism 7700 Sequence Detection System, Applied Biosystems) and final quantitation done using the comparative $C_T$ method (Leutenegger et al. (1999) Quantitative real-time PCR for the measurement of feline cytokine mRNA; *Veterinary Immunology and Immunopathology* 71:291-305) reported as relative transcription to an internal calibrator (GAPDH). Cytokine levels between affected samples and unaffected controls were compared by paired t-test, with P≦as a cutoff for establishing statistical significance.

Example 12

Genetic Studies and Molecular Virology

The rapid emergence of a novel FCV-associated clinical syndrome suggested that new genetic FCV variants may be responsible. Caliciviruses are non-enveloped, positive-sense, single-stranded RNA viruses, and include FCV, rabbit hemorrhagic disease virus (RHDV), and vesicular exanthema of swine virus. VS-FCV particles are 32-35 nm with scalloped borders and surface indentations that are typical of Caliciviridae with a central, electron dense core 20 nm in diameter, and less electron-dense surround, with T=3 icosahedral symmetry. Like other members of the family Caliciviridae, FCV is prone to high mutation rates and minimal repair.

In order to determine whether there was a unique mutation that occurred in VS-FCV strains and that discriminated them from other "field strains", genetic studies were performed in the hypervariable region of the capsid and at the level of the whole genome. PCR was performed as described previously (Pedersen et al. (2000) An isolated epizootic of hemorrhagic-like fever in cats caused by a novel and highly virulent strain of feline calicivirus; *Veterinary Microbiology* 73:281-300) to obtain a 235 nucleotide amplicon in the viral capsid hypervariable region for sequencing of affected and unaffected cats. When isolates from the northern and southern California VS-FCV outbreaks were compared with VS-FCVs from North Carolina and Florida, F9 (the vaccine strain), and miscellaneous field strains, all isolates from the Los Angeles outbreak clustered within a single clade, genetically distinct from the strains used for comparison. VS-FCV strains from different regions did not all cluster together. Isolates of FCV-Kaos (from Los Angeles) were characterized by a three base pair deletion, but this deletion was missing in VS-FCVs from other outbreaks. Homology between sequences of FCV-Kaos and FCV-F9 was 73.4%, and homology between sequences of FCV-Kaos and FCV-Ari (from northern California) was 76.5%. FCV-Ari is very closely related to the vaccine strain.

The entire genome of FCV-Ari and FCV-Kaos was sequenced and compared with other genomes previously reported, including the vaccine strain genome. At this level, FCV-Ari continued to cluster with the vaccine and was quite distinct from FCV-Kaos, with only 80.3% homology between the two. The predicted amino acid translations for the three reading frames of FCV were compared. In the open reading frame 1 (ORF 1), there were only three VS-FCV-specific changes (i.e., consistent among the VS-FCV strains and distinct from all reported field or vaccine strains), such as: E→D at position 294, N→S at 1055, and T at 1314 (various amino acids in field strains). There were seven VS-FCV specific amino acid residues in the capsid gene, including E→K at 398, V→T at 430, T→V at 438, A→K at 448, D→E at 452, R→K or D at 581, and S→D at 592, and no consistent changes in ORF-3. All seven changes in the capsid occurred generally in the same region from 398-592. Interestingly, protein structure was predicted to differ in the capsid with one extra glycosylation site in the VS-FCVs compared with field strains.

Caliciviruses have a unique single structural capsid protein which functions in RNA and host cell attachment. The virus has numerous arch-like capsomeres, each of which is a capsid protein dimer. Novel receptor or other host-virus interactions may occur as a result of mutated capsid protein structure, particularly targeting epithelial or endothelial cells, and inducing vaccine resistance. The skin's endarterial circulation and unique local immune cell populations (particularly dendritic cells capable of secreting TNF-α) may provide additional targets for further evaluation of VS-FCV-host interactions.

Various modifications and variations of the present invention will be apparent to those skilled in the art without departing from the scope and spirit of the invention. Although the invention has been described in connection with specific preferred embodiments, it should be understood that the invention as claimed should not be unduly limited to to such specific embodiments. Indeed, various modifications of the described modes for carrying out the invention which are obvious to those skilled in the art are intended to be within the scope of the claims.

What is claimed is:

1. An isolated virulent systemic calicivirus (VS-FCV), wherein said virus causes a highly contagious hemorrhagic fever syndrome in cats with symptoms selected from the group consisting of high fever, edema, ulceration, hair loss, nasal and ocular discharge, anorexia, depression, and death, wherein treatment of said cats with an immunologically effective dose of FCV-F9 achieves substantially no protection against infection with VS-FCV; and wherein said VS-FCV comprises a capsid protein including lysine at amino acid position 448; glutamic acid at amino acid position 452; and lysine or aspartic acid at amino acid position 581 when optimally aligned with the capsid protein of SEQ ID NO:1.

2. An immunogenic composition for immunization against a viral infection caused by the VS-FCV of claim 1, wherein said immunogenic composition comprises an immunologically effective amount of said VS-FCV and a physiologically acceptable carrier.

3. The immunogenic composition of claim 2, further comprising an adjuvant.

4. The composition of claim 2, wherein said VS-FCV is killed.

5. The composition of claim 2, wherein said VS-FCV is attenuated.

6. The composition of claim 2, wherein said VS-FCV is partially inactivated.

7. The isolated virulent systemic calicivirus (VS-FCV) of claim 1, wherein the capsid protein further comprises lysine at amino acid position 399; threonine is at amino acid position 430; valine at amino acid position 438; and wherein said VS-FCV further comprises a glycosylation site including an asparagine at amino acid position 394.

8. The isolated virulent systemic calicivirus of claim 1, wherein the cap sid protein sequence is SEQ ID NO:2.

9. The isolated virulent systemic calicivirus of claim 1, wherein the capsid protein sequence is SEQ ID NO:3.

10. The isolated virulent systemic calicivirus of claim 1, wherein the capsid protein sequence is SEQ ID NO:4.

* * * * *

SEQUENCE LISTING

```
<160> NUMBER OF SEQ ID NOS: 4

<210> SEQ ID NO 1
<211> LENGTH: 671
<212> TYPE: PRT
<213> ORGANISM: Feline calicivirus
<220> FEATURE:
<223> OTHER INFORMATION: feline calcivirus (FCV) m86379 capsid protein

<400> SEQUENCE: 1

Met Cys Ser Thr Cys Ala Asn Val Leu Lys Tyr Tyr Asp Trp Asp Pro
  1               5                  10                  15

His Phe Lys Leu Val Ile Asn Pro Asn Asn Phe Leu Ser Val Gly Phe
             20                  25                  30

Cys Ser Asn Pro Leu Met Cys Cys Tyr Pro Glu Leu Leu Pro Glu Phe
         35                  40                  45

Gly Thr Val Trp Asp Cys Asp Arg Ser Pro Leu Glu Ile Tyr Leu Glu
```

-continued

```
            50                  55                  60
Ser Ile Leu Gly Asp Asp Glu Trp Ala Ser Thr Phe Asp Ala Val Asp
 65                  70                  75                  80

Pro Val Val Pro Pro Met His Trp Gly Ala Ala Gly Lys Ile Phe Gln
                 85                  90                  95

Pro His Pro Gly Val Leu Met His His Leu Ile Gly Lys Val Ala Ala
            100                 105                 110

Gly Trp Asp Pro Asp Leu Pro Leu Ile Arg Leu Glu Ala Asp Asp Gly
            115                 120                 125

Ser Ile Thr Ala Pro Glu Gln Gly Thr Met Val Gly Val Ile Ala
            130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
                180                 185                 190

Leu Gly Pro Leu Leu Asn Pro Tyr Leu Glu His Leu Ala Lys Leu Tyr
                195                 200                 205

Val Ala Trp Ser Gly Ser Ile Glu Val Arg Phe Ser Ile Ser Gly Ser
            210                 215                 220

Gly Val Phe Gly Gly Lys Leu Ala Ala Ile Val Pro Pro Gly Val
225                 230                 235                 240

Asp Pro Val Gln Ser Thr Ser Met Leu Gln Tyr Pro His Val Leu Phe
                245                 250                 255

Asp Ala Arg Gln Val Glu Pro Val Ile Phe Cys Leu Pro Asp Leu Arg
                260                 265                 270

Ser Thr Leu Tyr His Leu Met Ser Asp Thr Thr Ser Leu Val
            275                 280                 285

Ile Met Val Tyr Asn Asp Leu Ile Asn Pro Tyr Ala Asn Asp Ala Asn
            290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Ile Pro Ser Asp Leu Ile Pro Lys Thr Ser Ser Leu Trp Ile Gly Asn
                340                 345                 350

Arg Tyr Trp Ser Asp Ile Thr Asp Phe Val Ile Arg Pro Phe Val Phe
            355                 360                 365

Gln Ala Asn Arg His Phe Asp Phe Asn Gln Glu Thr Ala Gly Trp Ser
            370                 375                 380

Thr Pro Arg Phe Arg Pro Ile Ser Val Thr Ile Thr Glu Gln Asn Gly
385                 390                 395                 400

Ala Lys Leu Gly Ile Gly Val Ala Thr Asp Tyr Ile Val Pro Gly Ile
                405                 410                 415

Pro Asp Gly Trp Pro Asp Thr Thr Ile Pro Gly Glu Leu Ile Pro Ala
                420                 425                 430

Gly Asp Tyr Ala Ile Thr Asn Gly Thr Gly Asn Asp Ile Thr Thr Ala
            435                 440                 445

Thr Gly Tyr Asp Thr Ala Asp Ile Ile Lys Asn Asn Thr Asn Phe Arg
            450                 455                 460

Gly Met Tyr Ile Cys Gly Ser Leu Gln Arg Ala Trp Gly Asp Lys Lys
465                 470                 475                 480
```

-continued

```
Ile Ser Asn Thr Ala Phe Ile Thr Thr Ala Thr Leu Asp Gly Asp Asn
                485                 490                 495

Asn Asn Lys Ile Asn Pro Cys Asn Thr Ile Asp Gln Ser Lys Ile Val
            500                 505                 510

Val Phe Gln Asp Asn His Val Gly Lys Lys Ala Gln Thr Ser Asp Asp
        515                 520                 525

Thr Leu Ala Leu Leu Gly Tyr Thr Gly Ile Gly Glu Gln Ala Ile Gly
    530                 535                 540

Ser Asp Arg Asp Arg Val Val Arg Ile Ser Thr Leu Pro Glu Thr Gly
545                 550                 555                 560

Ala Arg Gly Gly Asn His Pro Ile Phe Tyr Lys Asn Ser Ile Lys Leu
                565                 570                 575

Gly Tyr Val Ile Arg Ser Ile Asp Val Phe Asn Ser Gln Ile Leu His
            580                 585                 590

Thr Ser Arg Gln Leu Ser Leu Asn His Tyr Leu Leu Pro Pro Asp Ser
        595                 600                 605

Phe Ala Val Tyr Arg Ile Ile Asp Ser Asn Gly Ser Trp Phe Asp Ile
    610                 615                 620

Gly Ile Asp Ser Asp Gly Phe Ser Phe Val Gly Val Ser Gly Phe Gly
625                 630                 635                 640

Lys Leu Glu Phe Pro Leu Ser Ala Ser Tyr Met Gly Ile Gln Leu Ala
                645                 650                 655

Lys Ile Arg Leu Ala Ser Asn Ile Arg Ser Pro Met Thr Lys Leu
            660                 665                 670

<210> SEQ ID NO 2
<211> LENGTH: 668
<212> TYPE: PRT
<213> ORGANISM: Feline calicivirus
<220> FEATURE:
<223> OTHER INFORMATION: virulent systemic feline calcivirus (VS-FCV)
      FCV-Ari capsid protein

<400> SEQUENCE: 2

Met Cys Ser Thr Cys Ala Asn Val Leu Lys Tyr Tyr Gly Trp Asp Pro
  1               5                  10                  15

His Phe Arg Leu Thr Ile Asn Pro Asn Arg Phe Leu Ser Val Gly Phe
                20                  25                  30

Cys Asp Lys Pro Leu Ile Cys Cys Tyr Pro Glu Leu Leu Pro Glu Phe
            35                  40                  45

Gly Thr Val Trp Asp Cys Asp Gln Ser Pro Leu Gln Ile Tyr Leu Glu
        50                  55                  60

Ser Ile Leu Gly Asp Asp Glu Trp Ser Ser Thr Tyr Asp Ala Ile Asp
 65                  70                  75                  80

Pro Cys Val Pro Pro Met His Trp Asp Glu Ala Gly Lys Ile Phe Gln
                85                  90                  95

Pro His Pro Gly Val Leu Met His His Leu Ile Asn Glu Val Ala Lys
                100                 105                 110

Gly Trp Asp Pro Ser Leu Pro Asn Phe Arg Leu Glu Ala Asp Asp Gly
            115                 120                 125

Ser Ile Thr Thr Pro Glu Gln Gly Thr Met Val Gly Gly Val Ile Ala
        130                 135                 140

Glu Pro Ser Ser Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
```

```
                165                 170                 175
Asn Trp Ser Thr Ser Glu Thr Gln Gly Lys Ile Leu Phe Lys Gln Ser
                180                 185                 190
Leu Gly Pro Leu Leu Asn Pro Tyr Leu Ser His Leu Ala Lys Leu Tyr
                195                 200         205
Val Ala Trp Ser Gly Ser Ile Glu Val Arg Phe Ser Ile Ser Gly Ser
        210                 215                 220
Gly Val Phe Gly Gly Lys Leu Ala Ala Ile Val Pro Pro Gly Ile
225                 230                 235                 240
Asp Pro Val Gln Ser Thr Ser Met Leu Gln Tyr Pro His Val Leu Phe
                245                 250                 255
Asp Ala Arg Gln Val Glu Pro Val Ile Phe Ser Ile Pro Asp Leu Arg
                260                 265                 270
Ser Thr Leu Tyr His Phe Met Ser Asp Thr Asp Thr Ser Leu Ala
                275                 280                 285
Ile Met Val Tyr Asn Asp Leu Ile Asn Pro Tyr Ala Asn Asp Ser Asn
                290                 295                 300
Ser Ser Gly Cys Ile Val Thr Val Glu Thr Lys Pro Gly Pro Asp Phe
305                 310                 315                 320
Lys Phe His Leu Leu Lys Pro Pro Gly Ser Met Leu Thr His Gly Ser
                325                 330                 335
Val Pro Ser Asp Leu Ile Pro Arg Ser Ser Tyr Trp Thr Gly Asn
                340                 345                 350
Arg His Trp Thr Asp Ile Thr Gly Phe Val Ile Arg Pro Phe Val Phe
                355                 360                 365
Gln Ala Asn Arg His Phe Asp Phe Asn Gln Glu Thr Ala Gly Trp Ser
                370                 375                 380
Ser Pro Arg Phe Arg Pro Ile Ser Ile Asn Ile Ser Val Glu Lys Ala
385                 390                 395                 400
Ala Lys Leu Gly Thr Gly Val Ala Thr Asp Tyr Ile Val Pro Gly Ile
                405                 410                 415
Pro Asp Gly Trp Pro Asp Thr Thr Ile Pro Glu Lys Leu Thr Pro Ala
                420                 425                 430
Gly Asp Tyr Ala Ile Val Asp Gly Ser Gly Asn Asp Ile Thr Thr Lys
                435                 440                 445
Asp Lys Tyr Glu Ser Ala Asp Val Ile Lys Asn Asn Thr Asn Phe Arg
                450                 455                 460
Gly Met Tyr Ile Cys Gly Ser Leu Gln Arg Ala Trp Gly Asp Lys Lys
465                 470                 475                 480
Ile Ser Asn Thr Ala Phe Ile Thr Thr Gly Thr Val Lys Asp Asn Ser
                485                 490                 495
Ile Ile Pro Ser Asn Thr Ile Asp Gln Thr Lys Ile Thr Val Phe Gln
                500                 505                 510
Asp Thr His Val Gly His Asp Pro Gln Thr Ser Asp Thr Leu Ala
                515                 520                 525
Leu Leu Gly Tyr Thr Gly Ile Gly Glu Glu Ala Ile Gly Ala Asp Arg
                530                 535                 540
Asp Arg Val Val Arg Ile Ser Val Leu Pro Glu Thr Gly Ala Arg Gly
545                 550                 555                 560
Gly Asn His Pro Ile Phe Tyr Arg Asn Ser Ile Lys Leu Gly Tyr Val
                565                 570                 575
Leu Lys Asp Ile Asp Val Phe Asn Ser Gln Ile Leu His Thr Ser Lys
                580                 585                 590
```

```
Gln Leu Ser Leu Asn His Tyr Leu Leu Ser Pro Asp Ser Phe Ala Val
        595                 600                 605

Tyr Arg Ile Thr Asp Ser Asn Gly Ser Trp Phe Asp Ile Gly Ile Asp
    610                 615                 620

Asn Asp Gly Phe Ser Phe Val Gly Val Ser Tyr Ile Gly Asn Leu Glu
625                 630                 635                 640

Phe Pro Leu Thr Ala Ser Tyr Met Gly Ile Gln Leu Ala Lys Ile Arg
            645                 650                 655

Leu Ala Ser Asn Ile Arg Ser Gly Met Val Lys Ile
        660                 665

<210> SEQ ID NO 3
<211> LENGTH: 667
<212> TYPE: PRT
<213> ORGANISM: Feline calicivirus
<220> FEATURE:
<223> OTHER INFORMATION: virulent systemic feline calcivirus (VS-FCV)
      FCV-Kaos capsid protein

<400> SEQUENCE: 3

Met Cys Ser Thr Cys Ala Asn Val Leu Lys Tyr Tyr Asp Trp Asp Pro
1               5                   10                  15

Leu Phe Arg Leu Ile Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Glu Ser Thr Tyr Glu Ala Val Asp
65                  70                  75                  80

Pro Val Val Pro Pro Met His Trp Asp Thr Ala Gly Lys Ile Phe Gln
                85                  90                  95

Pro His Pro Gly Val Leu Met His Tyr Leu Ile Gly Glu Val Ala Lys
            100                 105                 110

Ala Trp Asp Pro Asn Leu Pro Leu Phe Arg Leu Glu Ala Asp Asp Gly
        115                 120                 125

Ser Ile Thr Thr Pro Glu Gln Gly Thr Met Val Gly Gly Val Ile Ala
    130                 135                 140

Glu Pro Ser Ala Gln Met Ser Thr Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Gly Pro Leu Leu Asn Pro Tyr Leu Glu His Leu Ser Lys Leu Tyr
        195                 200                 205

Val Ala Trp Ser Gly Ser Val Glu Val Arg Phe Ser Ile Ser Gly Ser
    210                 215                 220

Gly Val Phe Gly Gly Lys Leu Ala Ala Ile Val Val Pro Pro Gly Val
225                 230                 235                 240

Glu Pro Val Gln Ser Thr Ser Met Leu Gln Tyr Pro His Val Leu Phe
                245                 250                 255

Asp Ala Arg Gln Val Glu Pro Val Ile Phe Ser Ile Pro Asp Leu Arg
            260                 265                 270

Ser Ser Leu Tyr His Leu Met Ala Asp Pro Asp Pro Thr Tyr Leu Val
```

```
                    275                 280                 285
Ile Met Val Tyr Asn Asp Leu Ile Asn Pro Tyr Ala Asn Asp Ser Asn
    290                 295                 300

Ser Ser Gly Cys Ile Val Thr Val Glu Thr Lys Pro Gly Pro Asp Phe
305                 310                 315                 320

Lys Phe His Leu Leu Lys Pro Pro Gly Ser Met Leu Thr His Gly Ser
                325                 330                 335

Val Pro Ser Asp Leu Ile Pro Lys Ser Ser Leu Trp Ile Gly Asn
                340                 345                 350

Arg His Trp Thr Asp Ile Thr Asp Phe Val Ile Arg Pro Phe Val Phe
            355                 360                 365

Gln Ala Asn Arg His Phe Asp Phe Asn Gln Glu Thr Ala Gly Trp Ser
370                 375                 380

Thr Pro Arg Tyr Arg Pro Met Thr Ile Asn Ile Ser Gln Lys Lys Gly
385                 390                 395                 400

Glu Arg Leu Gly Ile Gly Ile Ala Thr Asp Tyr Ile Val Pro Gly Ile
                405                 410                 415

Pro Asp Gly Trp Pro Asp Thr Thr Ile Pro Glu Glu Leu Thr Pro Ala
                420                 425                 430

Gly Asp Tyr Ala Ile Val Asn Gly Thr Ser Asp Ile Ala Thr Lys Ala
            435                 440                 445

Gln Tyr Glu Ala Ala Thr Ile Ile Thr Asn Asn Thr Asn Phe Lys Ser
    450                 455                 460

Met Tyr Ile Cys Gly Ser Leu Gln Arg Ala Trp Gly Asp Lys Lys Ile
465                 470                 475                 480

Ser Asn Thr Ala Phe Ile Thr Thr Gly Lys Val Glu Gly Asn Lys Ile
                485                 490                 495

Thr Pro Ser Asn Lys Ile Asp Pro Thr Met Ile Ala Val Phe Gln Asp
                500                 505                 510

Asn His Val Asn Leu Glu Val Gln Thr Ser Asp Val Thr Leu Ala Thr
            515                 520                 525

Leu Gly Tyr Thr Gly Ile Gly Glu Glu Ala Ile Gly Ala Asp Arg Glu
530                 535                 540

Lys Val Val Arg Ile Ser Val Leu Pro Glu Thr Gly Ala Arg Gly Gly
545                 550                 555                 560

Asn His Pro Ile Tyr Tyr Lys Asn Lys Met Lys Leu Gly Tyr Val Ile
                565                 570                 575

Asp Gly Ile Asp Val Phe Asn Ser Gln Ile Leu His Thr Ser Arg Gln
                580                 585                 590

Leu Ser Leu Asn Asn Tyr Leu Leu Pro Pro Asp Ser Phe Ala Val Tyr
            595                 600                 605

Arg Ile Thr Asp Ala Asn Gly Ser Trp Phe Asp Ile Gly Ile Asp Ser
    610                 615                 620

Asp Gly Phe Ser Phe Val Gly Val Ser Ser Ile Gly Lys Leu Ile Ser
625                 630                 635                 640

Pro Leu Ser Ala Ser Tyr Met Gly Ile Gln Leu Ala Lys Ile Arg Leu
                645                 650                 655

Ala Ser Asn Ile Arg Ser Ser Met Thr Lys Leu
                660                 665

<210> SEQ ID NO 4
<211> LENGTH: 618
<212> TYPE: PRT
<213> ORGANISM: Feline calicivirus
```

```
<220> FEATURE:
<223> OTHER INFORMATION: virulent systemic feline calcivirus (VS-FCV)
      FCV-Bellingham capsid protein

<400> SEQUENCE: 4

Met Cys Ser Thr Cys Ala Asn Val Leu Lys Tyr Tyr Asn Trp Asp Pro
 1               5                  10                  15

His Phe Arg Leu Val Ile Asn Pro Asn Lys Phe Leu Ser Val Gly Phe
            20                  25                  30

Cys Asp Asn Pro Leu Met Cys Cys Tyr Pro Glu Leu Leu Pro Glu Phe
        35                  40                  45

Gly Thr Val Trp Asp Cys Asp Gln Ser Pro Leu Gln Ile Tyr Leu Glu
    50                  55                  60

Ser Ile Leu Gly Asp Asp Glu Trp Ser Ser Thr Tyr Glu Ala Ile Asp
65                  70                  75                  80

Pro Cys Val Pro Pro Met His Trp Asp Glu Ala Gly Lys Ile Phe Gln
                85                  90                  95

Pro His Pro Gly Val Leu Met His His Ile Ile Gly Glu Val Ala Lys
            100                 105                 110

Ala Trp Asp Pro Asn Leu Pro Asn Phe Arg Leu Glu Ala Asp Asp Gly
        115                 120                 125

Ser Ile Thr Thr Pro Glu Gln Gly Thr Val Gly Gly Val Ile Ala
    130                 135                 140

Glu Pro Ser Val Gln Met Ser Ala Ala Ala Asp Met Ala Thr Gly Lys
145                 150                 155                 160

Ser Val Asp Ser Glu Trp Glu Ala Phe Phe Ser Phe His Thr Ser Val
                165                 170                 175

Asn Trp Ser Thr Ser Glu Thr Gln Gly Lys Ile Leu Phe Lys Gln Ser
            180                 185                 190

Leu Arg Pro Leu Leu Asn Pro Tyr Tyr Pro His Val Leu Phe Asp Ala
        195                 200                 205

Arg Gln Val Glu Pro Val Ile Phe Thr Ile Pro Asp Leu Arg Ser Thr
    210                 215                 220

Leu Tyr His Leu Met Ala Asp Pro Glu Pro Thr Ser Leu Val Ile Met
225                 230                 235                 240

Ile Tyr Asn Asp Leu Ile Asn Pro Tyr Ala Asn Asp Ser Asn Ser Ser
                245                 250                 255

Gly Cys Ile Val Thr Val Glu Thr Lys Pro Gly Pro Asp Phe Lys Phe
            260                 265                 270

His Leu Leu Lys Pro Pro Gly Ser Met Leu Thr His Gly Ser Val Pro
        275                 280                 285

Cys Asp Leu Ile Pro Lys Ser Ser Leu Trp Ile Gly Asn Arg Phe
    290                 295                 300

Trp Ser Asp Ile Thr Asp Phe Val Ile Arg Pro Phe Val Phe Gln Ala
305                 310                 315                 320

Asn Arg His Phe Asp Phe Asn Lys Glu Thr Ala Gly Trp Ser Thr Pro
                325                 330                 335

Arg Phe Arg Pro Ile Thr Val Thr Ile Ser Gln Lys Glu Gly Glu Met
            340                 345                 350

Leu Gly Ile Gly Val Ala Thr Asp Tyr Ile Val Pro Gly Ile Pro Asp
        355                 360                 365

Gly Trp Pro Asp Thr Thr Ile Pro Asn Lys Leu Ile Pro Ala Gly Asp
    370                 375                 380

Tyr Ala Ile Thr Asn Gln Ser Gly Asn Asp Ile Gln Thr Lys Glu Glu
```

-continued

```
                385                 390                 395                 400
Tyr Glu Ser Ala Met Ile Ile Ser Asn Asn Thr Asn Phe Lys Ser Met
            405                 410                 415

Tyr Ile Cys Gly Ser Leu Gln Arg Ala Trp Gly Asn Lys Lys Val Ser
            420                 425                 430

Asn Thr Ala Phe Ile Thr Thr Ala Thr Val Lys Glu Asn Lys Leu Ile
            435                 440                 445

Pro Ser Asn Thr Ile Asp Gln Thr Lys Ile Ala Ile Phe Gln Asp Asn
            450                 455                 460

His Val Asn Arg Asp Val Gln Thr Ser Asp Asp Thr Leu Ala Leu Leu
465                 470                 475                 480

Gly Tyr Thr Gly Ile Gly Glu Glu Ala Ile Gly Ala Asp Arg Glu Lys
            485                 490                 495

Val Val Arg Ile Gly Val Leu Pro Glu Ala Gly Ala Arg Gly Gly Asn
            500                 505                 510

His Pro Ile Phe Tyr Arg Asn Ser Met Lys Leu Gly Tyr Val Ile Lys
            515                 520                 525

Ser Ile Asp Val Phe Asn Ser Gln Ile Leu His Thr Ser Arg Gln Leu
530                 535                 540

Ser Leu Asn Asn Tyr Leu Leu Ser Pro Asp Ser Phe Ala Val Asn Pro
545                 550                 555                 560

Thr Ile Asp Ser Asn Gly Ser Trp Trp Ser Ile Gly Ser Asp Ile Asp
                565                 570                 575

Ser Arg Ile Leu Val Asn Val Ser Thr Arg Gly Lys Lys Glu Phe Pro
            580                 585                 590

Leu Arg Ser Phe Cys Ser Glu Asn Gln Ser Gly Lys Ile Arg Ser Ala
            595                 600                 605

Ser Phe Ile Lys Thr Thr Arg Ser Lys Leu
610                 615
```